United States Patent [19]

Alley, Jr. et al.

[11] 4,103,550

[45] Aug. 1, 1978

[54] NOZZLE EXTRACTION PROCESS AND HANDLEMETER FOR MEASURING HANDLE

[75] Inventors: Vernon L. Alley, Jr., Newport News; Austin D. McHatton, Hampton, both of Va.

[73] Assignee: The United States of America as represented by the Administrator of the National Aeronautics and Space Administration, Washington, D.C.

[21] Appl. No.: 733,825

[22] Filed: Oct. 19, 1976

[51] Int. Cl.² .............................................. G01L 5/04
[52] U.S. Cl. ......................................... 73/159; 73/95
[58] Field of Search .................. 73/159, 95, 141 R, 98

[56] References Cited

U.S. PATENT DOCUMENTS

| | | | |
|---|---|---|---|
| 2,066,311 | 1/1937 | Appel et al. | 73/159 X |
| 2,630,710 | 3/1953 | Millson et al. | 73/159 |
| 3,026,726 | 3/1962 | Reading | 73/159 |
| 3,151,483 | 10/1964 | Plummer | 73/159 |
| 3,613,445 | 10/1971 | Dent et al. | 73/159 |
| 3,659,454 | 5/1972 | Stevenson | 73/159 |
| 3,777,557 | 12/1973 | Dunlap et al. | 73/95 |

OTHER PUBLICATIONS

Publ. "Review of Scientific Instruments", vol. 39, No. 8, Aug. 1968, Fabric Softness Meter, col. 1, p. 1239.
Publ. ". . . Physical Methods of Testing Textiles . . . ", Principles of Textile Testing, pp. 282-285.

*Primary Examiner*—Daniel M. Yasich
*Attorney, Agent, or Firm*—Howard J. Osborn; John R. Manning; Wallace J. Nelson

[57] ABSTRACT

Method and apparatus for quantitatively measuring the handle of fabrics and other flexible materials. Handle is that term used to refer to the qualities of drapability, flexibility, compressibility, foldability, stretchability, pliability, etc., possessed by fabrics and other flexible materials. In the present invention the handle of a material sample is quantified by measuring the force required to draw the sample through an orifice and expressing the resultant extractive force as a function of test apparatus geometry and the amount of sample drawn through the orifice to arrive at quantitative measure of handle, to be defined as handle modulus, for the sample in question.

30 Claims, 8 Drawing Figures

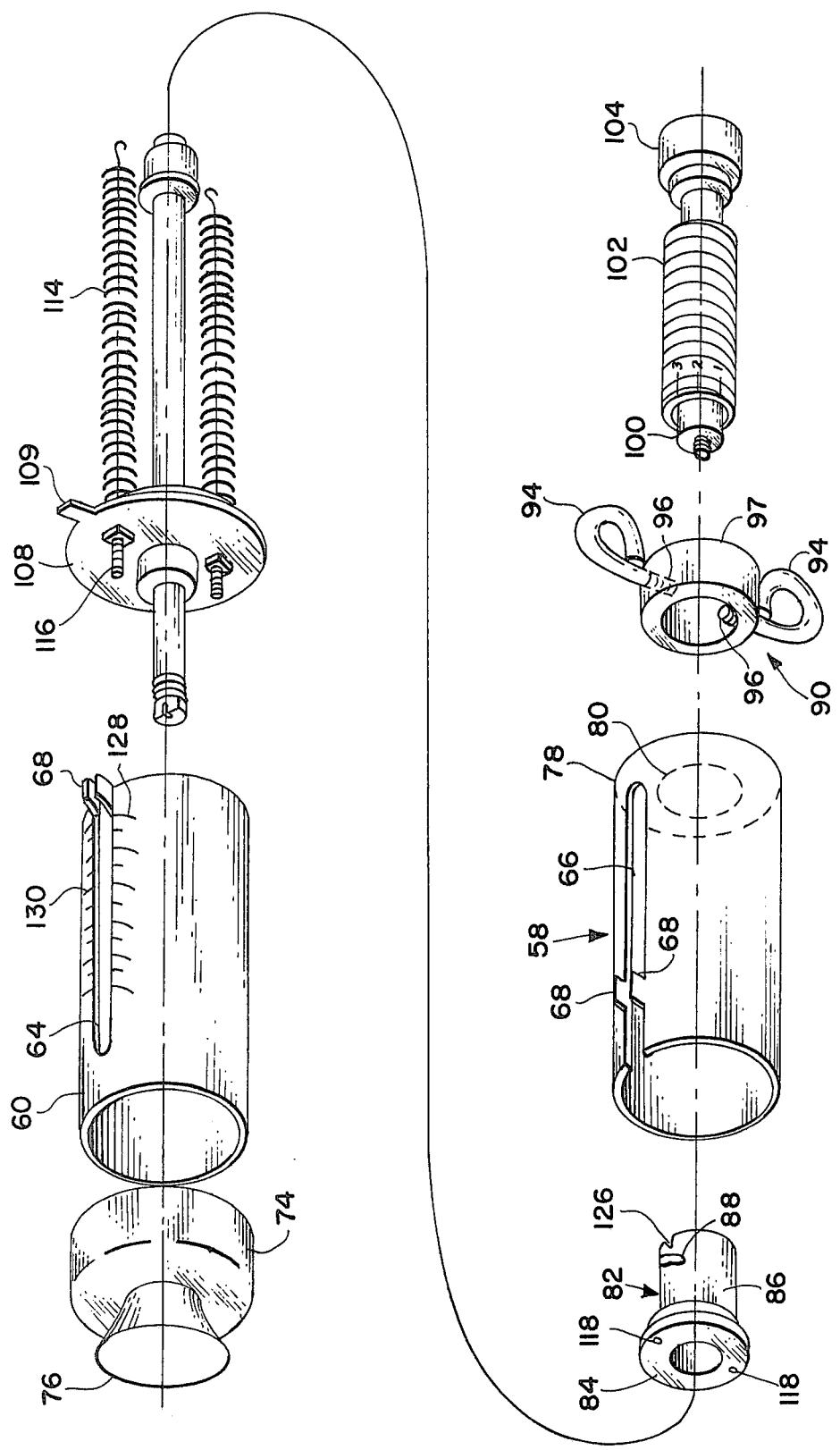

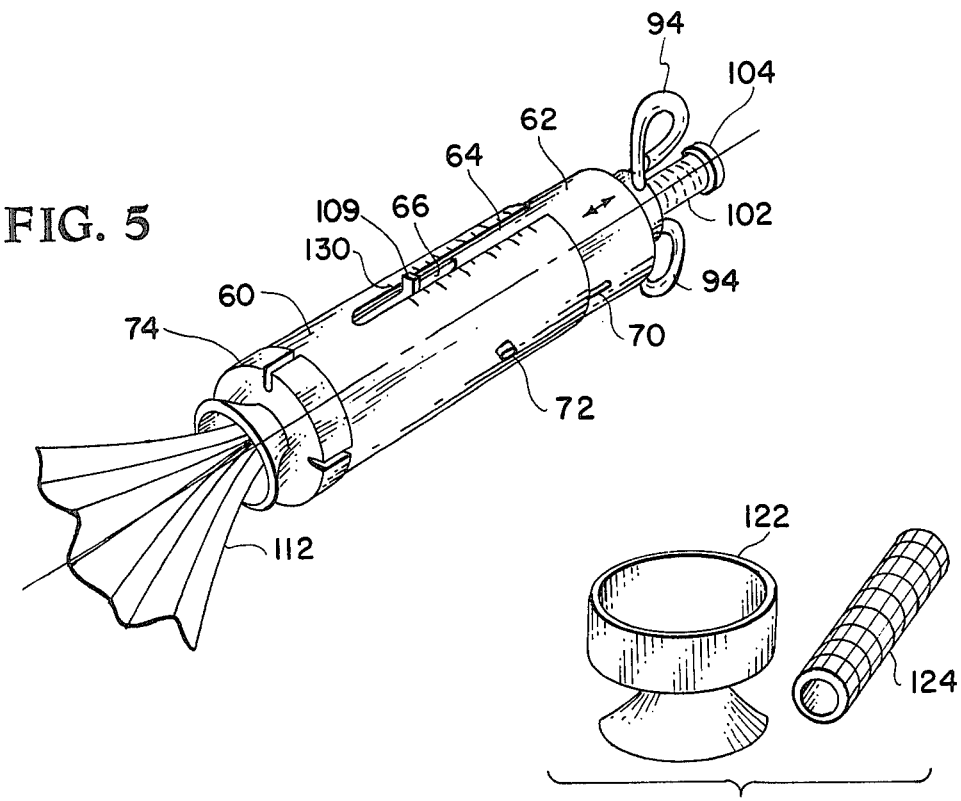
FIG. 5
FIG. 4a
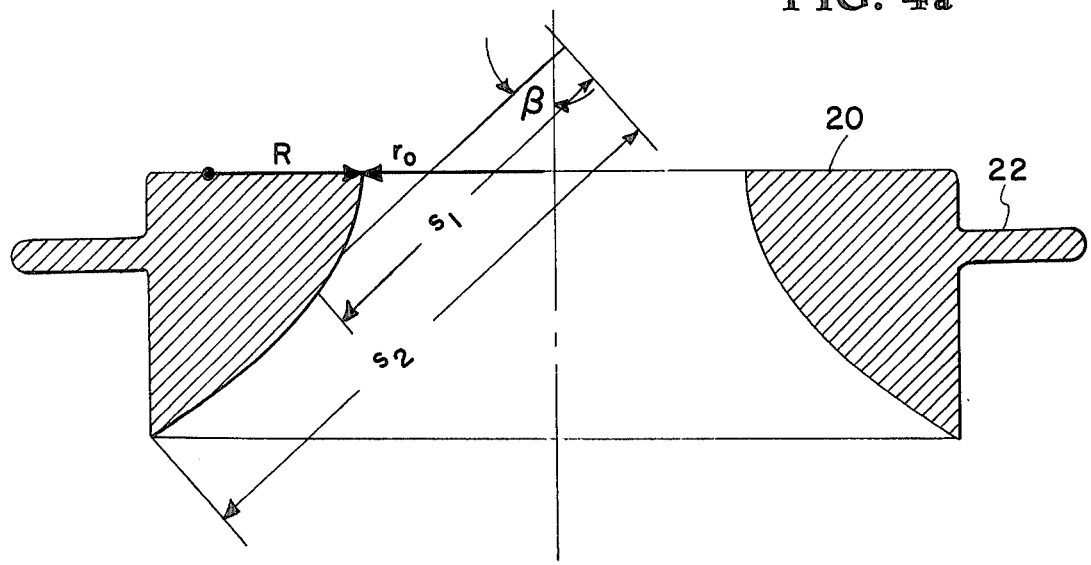
FIG. 7

NOZZLE EXTRACTION PROCESS AND HANDLEMETER FOR MEASURING HANDLE

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

This invention relates generally to the field of fabric and other flexible material testing and more particularly to methods and apparatus for quantitatively determining the handle of fabric and other flexible materials.

DESCRIPTION OF THE PRIOR ART

All fabrics and similar, sheet-like flexible materials possess in varying degrees the qualities of drapability, flexibility, compressibility, foldability, stretchability, pliability, etc. These properties are best defined by the textile term "handle." Good handle is the subjective or qualitative characteristic given to the feel of materials such as silks, nylons and bias materials. Materials having poor handle are generally stiff, crisp, boardy or semi-rigid.

At present, the determination of fabric handle remains largely subjective. Several presently available methods or apparatus assign quantitative numbers to one or two of the flexible, material qualities comprising handle; however, none yield a single quantitative figure, representative of all the qualities comprising handle, by which the handle and attendant characteristics of one material may be compared to those of another material.

With respect to handle testing, the American Society Testing Materials (ASTM) specifications refer to only two tests, both of which are directed to material stiffness though the interaction between fabric weight and fabric stiffness. A cantilever beam bending test and a loop distortion test are defined which give quantitative measures of how a fabric beam deflects under its own weight and how a fabric loop elongates due to gravity.

In *Physical Properties of Textile Fibers*, Morton and Hearle also discuss only stiffness as important to handle. They state that for a yarn of a given count or for a fabric of a given weight per unit area made from a given type of raw material, the resistance to bending diminishes as the fineness of the fabric increases. Thus, all other things being equal, the finer the fiber the better the handle of a given fabric.

Bosworth and Oliver, ("The Application of Multiple Factor Analysis to the Assessment of Fabric Handle," 49 Journal Textile Institute, November 1958), set forth a subjective-objective approach to evaluating fabric handle in which multiple samples are judged and ranked by a group of people. This subjective scoring is then augmented by standard tests for frictional properties, weight, thickness, stiffness as measured by the above described ASTM tests, flexural rigidity and bending modulus, hardness and cover factor. Although the test is more comprehensive than many, it is still largely subjective and does not necessarily yield repeatable results when different test personnel are involved, nor does this test lend itself to testing a variety of materials at differing times.

In 20 Textile Research Journal 539, Chu et al disclose a drapemeter which functions from a gravity-produced conical draping or deformation of a circular fabric specimen and assigns a numerical result thereto. This test method and apparatus considers only one of the several handle factors and thus the results do not necessarily correlate well with subjective determinations of handle.

In *Structural Mechanics of Fibers, Yarns and Fabrics*, Vol. 1, Hearle, Grosberg and Backer attempt to analyze handle for garment applications as a function of the shear and drape of fabrics. Hearle et al use the Chu et al drapmeter to analyze fabric drape, hence incorporating the above-mentioned drapmeter drawbacks. To the extent that garment fabric handle is dependent on drape and shear properties the Hearle et al method works reasonably well, but as in the Chu et al reference the method ignores the other handle factors and the results do not always correlate well with subjective measurements. Hearle et al does, however, analyze the drape phenomenon very well in pointing out that drape is for the most part dependent on fabric bending length and fabric shear resistance.

SUMMARY OF THE INVENTION

Accordingly, one object of the present invention is to provide a method and apparatus for quantitatively measuring the handle of fabrics and other flexible materials.

Another object of the present invention is to provide a numerical quantity, termed handle modulus, for expressing the measured handle of fabrics and other materials.

Another object of the present invention is to provide a method and apparatus for quantitatively measuring the handle of fabrics and other flexible materials which includes the effect that such qualitative properties as drapability, flexibility, compressibility, foldability, stretchability and pliability have on the handle of a given fabric.

Yet another object of the present invention is to provide a method and apparatus for quantitatively measuring the handle of a single type of fabric or other flexible materials which can be accomplished separately with respect to time and place from the testing of other types of material.

Still another object of the present invention is to provide a method and apparatus for quantitatively measuring the handle of a fabric or other flexible material relative to the handle of other fabrics and flexible materials.

A still further object of the present invention is to provide a method and apparatus for quantitatively measuring the handle of a fabric or other flexible material relative to the handle of a reference material.

A further object of the present invention is to provide an apparatus for quantitatively measuring the relative handle among a number of fabrics and flexible materials which corresponds to the maximum extent possible with a subjective determination of the relative handle properties of said number of fabrics and flexible materials.

According to one embodiment of the present invention, the foregoing and other objects are attained by providing a convergent nozzle detachably mounted on a tri-legged frame with the nozzle opening downward. The tri-legged frame is provided with a base plate which is attached to a standard laboratory force-displacement loading machine, such as an Instron ® machine, via a central female fitting. Extending downwardly from the frame base plate are three axially adjustable leveling studs which contact the Instron ® base plate and serve to level the frame and pre-tension the base plate attachment. Several interchangeable nozzles having geometrically similar contours but differing minimum throat areas are provided in order to test specimens of varying thicknesses. Each nozzle is provided with its own extraction rod sized diametrically such that it will give the maximum grip area when attached to the sample to be tested, yet still pass freely through the nozzle throat with the sample attached. The extraction rod appropriate to the nozzle being used is mounted in the Instron ® load cell above the nozzle such that it extends downwardly through and concentric with the nozzle.

A sample of flexible material to be measured is also provided. In order to assure uniform extraction through the nozzle, the sample is of circular configuration and is provided with a punched hole at its center so that it may be attached to its origin to the extraction rod. One end of each extraction rod is provided with a concave recess, threaded bore, domed washer and cap screw in order to facilitate attachment of the sample thereto. The radius of each sample should be less than the height of the test stand, i.e., the distance between the base plate and nozzle throat in order to prevent kinks and other undesired folds which may introduce error into the measurement of sample extraction forces.

In order to measure the handle characteristic of a given material, the sample is attached to the extraction rod and allowed to drape downwardly therefrom in a generally three-pedal conical geometry. The sample is then drawn through the nozzle while the force necessary to extract the sample through the nozzle is measured simultaneously with the axial displacement of the sample origin with respect to the nozzle throat. The handle modulus for the particular sample is then calculated from the obtained force-displacement data as a function of the force required to draw the sample through the orifice, the minimum throat area of the nozzle, the ratio of sample cross-sectional area to nozzle cross-sectional area at the throat of the nozzle, and the frictional and geometric properties of the nozzle used. By taking nozzle characteristics into consideration, the handle modulus is independent of the scale of the particular nozzle used and it is only necessary that a nozzle large enough so that the sample does not bind at its throat be selected.

BRIEF DESCRIPTION OF THE DRAWINGS

FIG. 4 is an exploded view of a portable handlemeter constructed according to the present invention;

FIG. 4a is an alternate embodiment of a nozzle and scale;

FIG. 5 is a perspective view of the assembled handlemeter of FIG. 4;

FIG. 7 is a schematic cutaway view of a handle measuring apparatus nozzle.

DESCRIPTION OF THE PREFERRED EMBODIMENT

Figures 1, 1A:
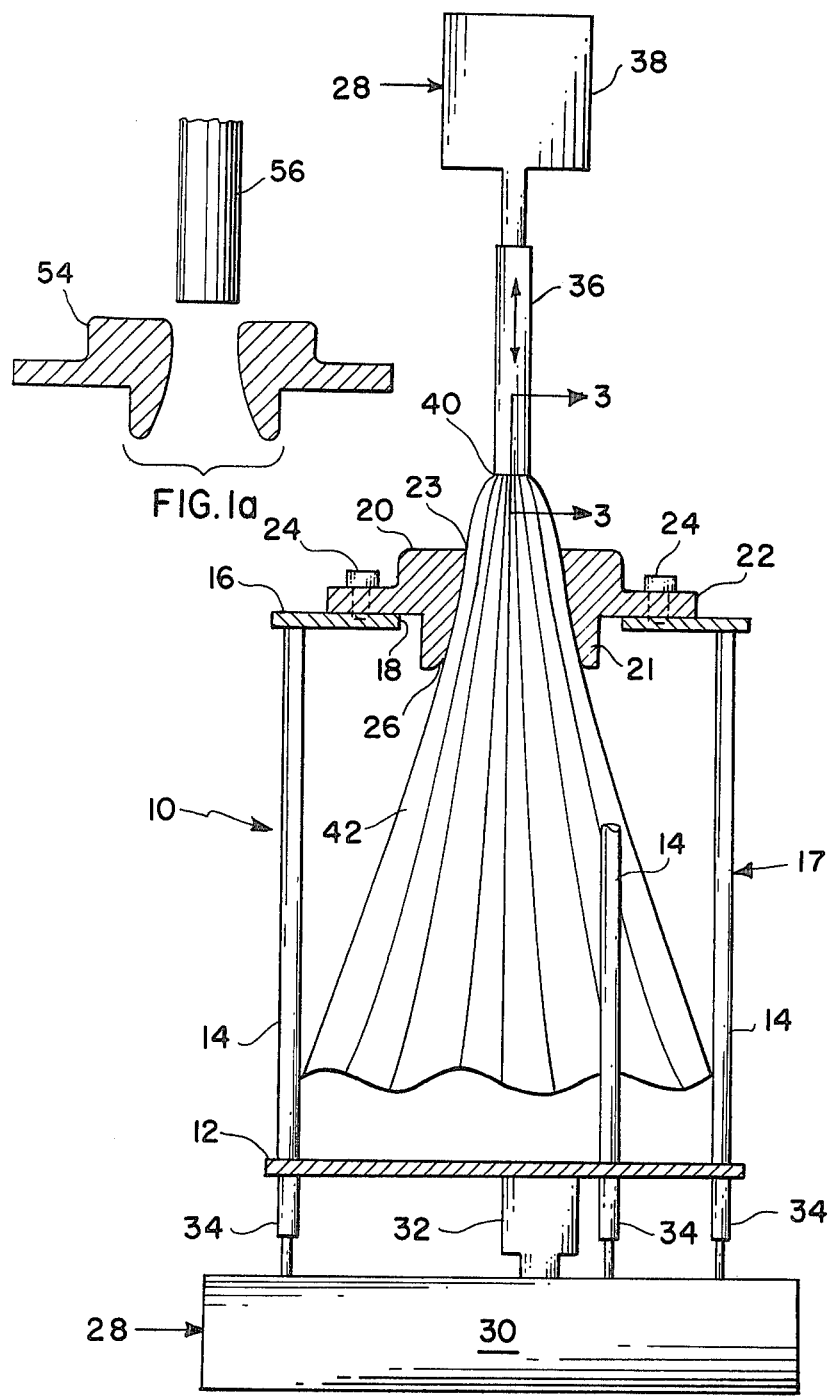
FIG. 1 is an elevation view of a laboratory handle measuring device constructed according to the present invention.
FIG. 1a is an elevational view of an alternate nozzle and extraction rod.

Referring now to the drawings wherein like reference charactors designate identical or corresponding parts, and more particularly to FIG. 1 wherein one embodiment of the present invention is depicted. It may be seen that the apparatus for measuring the handle modulus of fabrics or other flexible materials, indicated generally by the reference numeral 10, is comprised of a circular base plate 12 having three legs 14 extending upward therefrom. Upper plate 16 is also circular and is fixedly attached to legs 14 such that it is both parallel and concentric with base plate 12. Base plate 12, legs 14 and upper plate 16 comprise the apparatus frame, indicated generally by the reference numeral 17. Upper plate 16 is provided with a concentric circular aperture 18 to provide clearance for nozzle 20 which is detachably mounted thereon such that the skirt 21 of nozzle 20 extends downwardly through the plane of upper plate 16. Nozzle 20 is concentrically mounted in aperture 18 and is detachably secured to upper plate 16 by means of flange 22 and cap screws 24. Nozzle 20 is a convergent nozzle having a circular cross section with a truncated cone base section and an upper annulus section (see also FIG. 7) and it is mounted such that its minimum diameter or throat 23, is upwards with respect to base plate 12. Any suitable rigid material such as steel, aluminum, stainless steel or Teflon ® fluorocarbon polymer may be used in the construction of nozzle 20; however, the inner nozzle surface 26 should be highly polished or otherwise treated to minimize friction. Similarly frame 17 may be constructed of any suitable material such as steel, aluminum or stainless steel, and any number of legs 14 may be used; however, three legs are preferable as that number interferes least with the measurement operation while still affording adequate structural rigidity.

A standard laboratory load-displacement testing machine, such as an Instron ® machine indicated generally by the reference numeral 28, is provided to operate the measurement cycle and provide load and displacement data. Frame 17 is mounted on the lower cross beam 30 of Instron ® 28 by means of a standard Instron ® socket 32 which is fixedly attached to base plate 12. Three axially adjustable leveling studs 34 are fixedly attached to base plate 12 and extend downwardly therefrom to bear against cross beam 30. Leveling studs 34 serve to level frame 17 and preload it with respect to cross beam 30 in order to insure a secure connection. Sample extraction rod 36 is mounted on Instron ® load cell 38 such that its axis is concentric with the axis of nozzle 20. When load cell 38 is actuated, extraction rod 36 may be translated axially from a lower position at which the lower end 40 of extraction rod 36 is level with the bottom of nozzle skirt 21 to an upper position at which extraction rod end 40 is removed from the top of nozzle 20 a distance greater than the length of frame legs 14.

Figure 2:
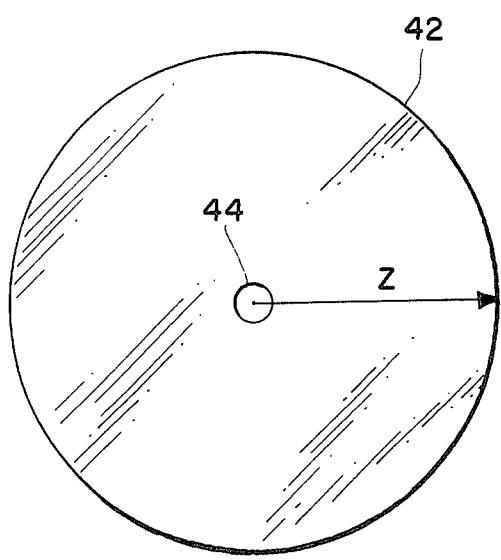
FIG. 2 is a plan view of a sample of flexible material to be tested.

FIG. 2 depicts a sample 42 of fabric or other flexible material to be tested. Sample 42 is circular in configuration and is provided with a punched hole 44 at its origin in order to facilitate attachment to extraction rod 36. The radius Z of sample 42 is less than the length of frame legs 14 in order to prevent kinks and other undesirable folding due to interference with the base plate 12 which may induce unnecessary deviations in the extraction force measurement procedure.

Figure 3:
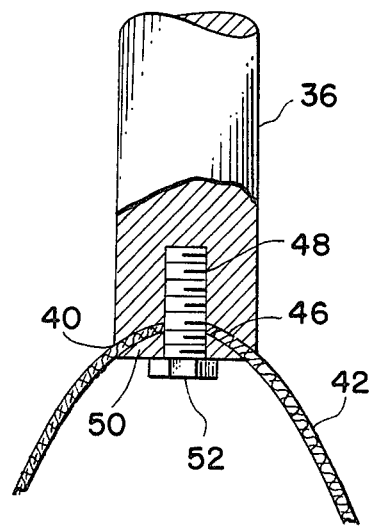
FIG. 3 is a sectional view taken along line 3—3 of FIG. 1.

Referring now to FIG. 3, the lower end 40 of extraction rod 36 is provided with a concave recess 46, threaded bore 48, convex washer 50 and cap screw 52 for purposes of attaching sample 42 to the extraction rod. Cap screw passes through hole 44 in sample 42 thereby assuring that the sample is correctly centered. When attached in the above manner to extraction rod 30, sample 42 hangs in a generally conical shape. It is preferable that sample 42 be arranged while it is hanging in a generally three pedal conical geometry free from kinks in order to assure a uniform extraction.

An additional nozzle and extraction rod, fully interchangeable with nozzle 20 and extraction rod 36, are provided in order to verify the valid region of test results and to more easily accommodate test samples of differing thicknesses. With respect to nozzle contour, the additional nozzle is a scaled up version of nozzle 20, i.e., both nozzles have geometrically similar contours but the minimum cross section, or throat, area of the additional nozzle is larger than that of nozzle 20. As will be explained hereinbelow, nozzle size has no effect on the determination of hand modulus of a given sample provided that the nozzle is at least small enough to restrict the passage of the sample tested and not so small that the sample binds or chokes in the nozzle during extraction.

In order to insure a more uniform extraction process, nozzles 20 and 54 are provided with extraction rods 36 and 56, respectively, matched to their throat sizes. Extraction rods 36 and 56 are sized diametrically such that they will give the maximum grip area when attached to a sample, yet will still pass freely through their respective nozzle throats with a sample attached.

Instron ® load displacement machine 28 serves three functions in the present invention. Firstly, it provides the upward axial movement of extraction rod 36 necessary to draw sample 42 through nozzle 20. Secondly, and thirdly, Instron ® 28 measures the extraction force required to draw sample 42 through nozzle 20 and measure the axial displacement of the sample origin, clamped at the end 40 of extraction rod 36, with respect to the throat 23 of nozzle 20.

An alternate, portable embodiment of the present invention is shown in FIGS. 4 and 5. This embodiment, which may be referred to as a portable handlemeter and is indicated generally by reference numeral 58, is completely self-contained and hand operated, therefore, it is suitable for use in the field for testing the handle modulus of various flexible materials.

The body of handlemeter 58 is a hollow, two-part, cylindrical telescoping assembly comprised of a nozzle section 60 and a handle section 62 slidably disposed within nozzle section 60. Sections 60 and 62 may be constructed of any workable rigid material such as steel, aluminum, plastic or stainless steel. Nozzle section 60 and handle section 62 are provided with axial slots 64 and 66, respectively, which are alined with each other when the two sections are assembled. In order to prevent relative rotation between nozzle section 60 and handle section 52, slot 66 is provided with a pair of tabs 68 which slidably engage slot 64. Slot 64 is also provided with a bendable tab 68 which is bent flush with the surface of nozzle section 60 after the sections 60 and 62 are assembled. Tab 68 prevents the two sections from separating upon maximum axial extension.

An alternate means of preventing relative rotation and axial separation of sections 60 and 62 is shown in FIG. 5 wherein handle section 62 is provided with a second axial slot 70 which has no open end as do slots 64 and 66. Thumb screw 72 is threadably mounted in nozzle section 60 and extends therethrough into sliding engagement with slot 70.

Nozzle 74 is detachably mounted on nozzle section 60 by frictional engagement or other suitable means such that the nozzle throat is concentric with nozzle section 60 and handle section 62. Nozzle 74 is of convergent geometry and circular cross section and is mounted with its maximum diameter facing outward. As in the embodiment of FIG. 1, nozzle 74 may be constructed of any suitable rigid material such as steel, aluminum, stainless steel or Teflon ® fluorocarbon polymer. The inner nozzle surface 76 should be highly polished or otherwise treated to minimize friction.

Handle section 62 is provided with a bottom 78 having a circular hole 80 therein. Hole 80 is concentric with handle section 62 and receives a shouldered bushing, indicated generally by the reference numeral 82. Bushing 82 is constructed of Teflon ® fluorocarbon polymer or other suitable low-friction compound, and is mounted in handle section 62 from the inside such that flange 84 bears against the inner surface of bottom 78 and bushing barrel 86 protrudes outward from hole 80. Bushing barrel 86 is provided with a pair of diametrically opposed detent grooves, one of which is shown at 88. A handle assembly, indicated generally by the reference numeral 90, engages that portion of bushing barrel 86 which protrudes from hole 80, thus bushing 82 is held in place in handle section 62 by means of flange 84 and handle assembly 90.

Handle assembly 90 is comprised of a collar 92, a pair of finger grip pins 94 and a pair of diametrically opposed, spring-loaded detent pins 96. As collar 92 is slipped over bushing barrel 86, detent pins 96 engage grooves 88. The engagement of handle assembly 90 with bushing barrel 86 is such that collar 92 is firmly affixed to bushing barrel 86 in an axial direction but is freely rotatable with respect to barrel 86 through an arc of approximately 30°. Upon attempting to rotate collar 90 past its 30° arc of free movement, detent pins 96 begin to ride out of detent grooves 86, thus compressing bushing barrel 86 radially inward. As will be explained hereinbelow, this radial compression of bushing barrel 86 serves as a means to lock bushing 82 with respect to extraction rod 98, how to be explained.

Extraction rod 98 is slidably disposed in bushing 82 such that it is concentric with handle section 62, nozzle section 60 and nozzle 74. Extraction rod 98 is provided with a scale stud extension 100 which threadably engages its handle end. Scale stud 100 is of smaller diameter than extraction rod 98 and is fitted with a cylindrical force measurement scale 102 and a knurled knob 104. The outside diameter of cylindrical scale 102 is equal to the diameter of that portion of extraction rod 98 slidably disposed in bushing 82, therefore it may be seen that scale 102 may slide inside bushing 82. Extraction rod 98 is also provided with a fixedly mounted thrust washer 106 which serves to limit the outward axial movement of the extraction rod with respect to handle section 62.

Indicator disc 108 is also fixedly mounted on extraction rod 98. Indicator disc 108 is provided with an indicator tab 109 which protrudes radially through slot 64 in nozzle assembly 60. Indicator tab 109 is constructed of Teflon ® fluorocarbon polymer or other suitable material in order to minimize friction with slot 64. Indicator tab 109 serves as a means of indicating the relative displacement of extraction rod 98 with respect to the throat of nozzle 74, as will be hereinbelow explained. The nozzle end of extraction rod 98 is provided with a concave recess, a convex washer 110 and specimen screw 111 similar to those illustrated in FIG. 3, for purpose of attaching test sample 112 thereto.

A pair of extraction force measurement springs 114 are connected at one end to indicator disc 108 by means of threaded adjustment studs 116 and are connected at their other end to bushing flange 84 by means of holes 118. Studs 116 are adjusted such that extraction rod 98 is zeroed with respect to nozzle 74 when the handlemeter is at rest. Extraction rod 91 is zeroed when concave end 120 in the same plane as the throat of nozzle 74. Springs 114 serve as a spring scale by which the force necessary to drawn a sample 112 of fabric or other flexible material to be measured on scale 102. Consequently, the spring rate of springs 114 must be known and scale 102 must be calibrated from the springs and nozzle used.

An extra nozzle 122 (FIG. 4a) of similar geometry to nozzle 74 but of larger throat area and an additional scale 124 are provided in order to test samples of heavier weights. If a wide variety of materials is to be tested, it may be necessary to use additional springs which would necessitate an additional scale for each possible spring-nozzle combination.

Force measurement scale 102 is of a spiral-like pattern having the coefficient of friction ($\mu$) between sample 112 and nozzle 74 plotted circumferentially versus handle modulus (H) which is plotted axially. Alternately, handle modulus ratio (H/$\overline{\text{H}}$) may be plotted axially in lieu of handle modulus. In calibrating scale 102, extraction force is converted to handle modulus or handle modulus ratio as will be explained below. Scale 102 is read from a reference mark 126 on bushing 82 as will also be explained hereinbelow.

Displacement scales 128 and 130 are provided adjacent to nozzle section slot 64 and are read by means of indicator tab 109. Scales 128 and 130 calibrated in terms of the displacement of extraction rod end 120 with respect to the throat of the particular nozzle used needed for a given sample effective thickness to yield a throat packing ratio of 0.07.

Packing ratio at the nozzle throat ($P_o$) is defined as the ratio of sample cross sectional area to nozzle cross sectional area at the throat of the nozzle. Clearly a different scale is needed for each nozzle used, hence scale 128 is calibrated for use with nozzle 74 and scale 130 is calibrated for use with nozzle 122.

As in the embodiment of FIG. 1, sample 112 is circular in configuration and is attached to extraction rod 98 by means of a hole punched at its origin. The radius of sample 112 is larger than the maximum stroke of handlemeter 58 in order to prevent it from being drawn completely or partially through the nozzle.

OPERATION

In operation in the case of the embodiment of FIG. 1, the sample of fabric or other material to be tested 42 is secured at hole 44 to extraction rod 36 by means of cap screw 52 and screw washer 50, such that sample 52 hangs through the below nozzle 20 in a generally conical shape. In order to assure a uniform and error-free extraction process, the conical skirt of sample 42 is arranged in a generally three pedal conical geometry. Extraction rod 36 is then positioned such that extraction rod end 40 is in the same plane as nozzle throat 23 in order to zero the displacement scale of Instron® 28. In the case of the convergent nozzles 20 and 54 used in the present invention, the nozzle throat, (i.e., that region of the nozzle having the smallest diameter) is level with the top of the nozzle.

Once the Instron® displacement scale is zeroed, load cell 38 is activated to extract sample 42 upwards through nozzle 20. During the extraction process, extraction force and extraction rod displacement are simultaneously measured. If it is desired to verify results, the entire process outlined above may be repeated using nozzle 54 and extension rod 56.

Figure 6:
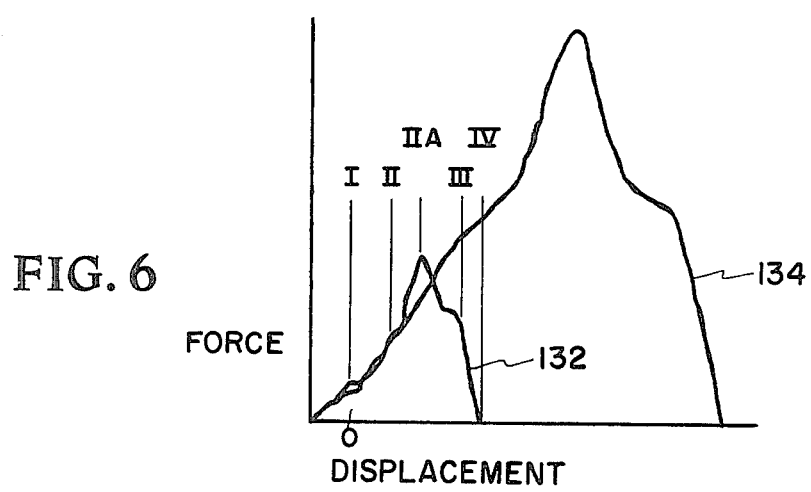
FIG. 6 is a schematic view of a typical handle measuring apparatus force displacement curve.

After completion of both extraction processes, the resulting force displacement data is plotted as shown in FIG. 6. Curve 132 displays the results of the extraction process using the smaller nozzle 20, and curve 134 depicts the results obtained from using larger nozzle 54. In order to illustrate extraction phenomena, curve 132 has been divided into five phases as follows: Phase I is an initiating phase where specimen 42 is first drawn into nozzle 20 and forced to press against the nozzle wall; Phase II is the valid portion of the test data where the curve is linear and sample 42 is in full contact with the entirety of the nozzle wall; Phase IIA represents a plume phenomenon where the skirt of sample 42 begins to billow, and shear forces develop in sample 42 resulting in higher extraction forces; Phase III represents that portion of the extraction process when sample 42 ceases to be completely in contact with the nozzle wall; and Phase IV represents the abrupt exit of the sample from the nozzle throat. Curve 134 exhibits the same general phase characteristics.

It should be noted that the slope of the Phase II region of curve 132 is practically identical with the slope of the corresponding region of curve 134, and in fact the two curves are partially coincident. This coincidence of slope defines the region of the force-displacement curves which are valid for handle measurement, and also gives proof of the fact that handle modulus measurement is independent of the scale of the nozzles used within the valid test range.

Once the force displacement data has been collected, the measured handle of sample 42 is expressed in terms of a coefficient termed handle modulus having units of force per unit area. Handle modulus is a function of extraction force, the throat area of the nozzle used, the compaction ratio of the sample within the nozzle throat, i.e., the ratio of sample cross-sectional area to nozzle cross-sectional area at the throat of the nozzle; and the frictional and geometric properties of the nozzle. The relationship of handle modulus to these parameters may be expressed mathemetically as follows:

$$H = \frac{1}{A_o N} \frac{dF}{dPo} = \frac{1}{2Nt_e N} \frac{dF}{dh}$$

where
 H = handle modulus (force/unit area)
 $A_o$ = area of nozzle throat
 F = extraction force
 Po = packing ratio at nozzle throat
 N = the sum of the frictional and geometric properties of the nozzle, (dimensionless) = $N_1 + \mu N_2$
 $t_e$ = effective thickness of sample 42 = (true volume of sample/area)
 h = extraction distance of same 42 from the plane of the nozzle throat As may be seen from the above equation, the required raw data from the extraction operation in $dF/dh$, of the slope of the force displacement curve. In the portable handlemeter embodiment, $dF/dh$ is approximated by $F/h$. By way of illustrative example, a sample of uncoated Nomex ® fabric having an effective thickness ($t_e$) of 59.1 μm extracted through a nozzle having a 5 cm throat radius and yielded an extraction force of 6.08 N at a 10 cm rxtraction displacement. Substituting the above number into the handle modulus formula results in a handle modulus of 4.49 N/cm².

As hereinabove explained, the packing or compaction ratio at the nozzle $P_o$ is the ratio of sample cross-sectional area to nozzle cross-sectional area at the throat of the nozzle. Expressed mathematically:

$$P_o = \frac{2(\frac{d}{2} + h) t_e}{r_o^2}$$

where
$d$ = diameter of extraction rod
$r_o$ = radius of the nozzle throat

As also stated hereinabove, $N = N_1 + \mu N_2$ wherein N is the nozzle characteristic or the sum of the frictional and geometric properties of the nozzle used. $N_1$ is that part of the nozzle characteristic independent of friction and dependent on the nozzle teometry, and $N_2$ is that part of the nozzle characteristic dependent on friction between the nozzle and sample. The Greek letter $\mu$ refers to the coefficient of friction between the nozzle surface and the sample, and is best determined experimentally or from existing friction-coefficient tables. FIG. 7 illustrates those nozzle parameters necessary to calculate N, using a convergent nozzle similar to nozzle 20 as an illustrative example. Expressed mathematically:

$$N_1 = 2 \left[ \frac{1}{1 + \frac{r_o}{R}} \ln \frac{1 + \frac{r_o}{R} - \cos\beta}{\frac{r_o}{R} \cos\beta} + \frac{1}{\cos\beta} \ln \frac{s_2}{s_1} \right]$$

where
$R$ = radius of nozzle annulus at nozzle throat
$\beta$ = one-half nozzle cone included angle (radians)
$s_1$ = distance from nozzle cone apex to small end of cone
$s_2$ = distance from nozzle cone apex to large end of cone
and $$N_2 = 2 \left[ \frac{1}{\sin\beta} \ln \frac{s_2}{s_1} + \frac{2}{\sqrt{\left(2 + \frac{r_o}{R}\right)\frac{r_o}{R}}} \tan^{-1}\left(\sqrt{\frac{2 + \frac{r_o}{R}}{\frac{r_o}{R}}} \tan \frac{1}{2}\beta\right) \right]$$

It should be noted that the nozzle characteristic $N_1$ and $N_2$ are independent of the scale of the nozzle but are dependent on the geometric properties of the nozzle annulus and truncated cone components.

The apparatus of the present invention may also be used to determine relative handle data by comparing the handle modulus of a given sample to that of a reference material. Relative handle data may be expressed in the form of a unitless ratio such as $H/\bar{H}$ where $\bar{H}$ represents the handle modulus of a reference material. Once recommended reference material is 1.1 oz/yd² nylon parachute cloth as specified by MIL - C - 70205. The handle modulus of this material is 2.17 newtons/cm² (3.15 lbs/in²).

One advantage of the handle modulus ratio method is that it obviates the necessity of analytically determining the nozzle characteristic N for each nozzle. One need only extract the reference material to determine extraction force and then solve the handle modulus equation for N. Another advantage of the handle ratio method is that the handle modulus ratio of a test material can be determined directly from a comparison of test material extraction force — displacement data — (i.e., slopes $dF/dh$) to reference material extraction force — displacement data.

The portable handle meter embodiment of the present invention is useful for either direct determination of handle modulus or of handle modulus ratio. In operation, test sample 112 is attached at its origin to extraction rod 98, and the meter is zeroed such that end 120 of extraction rod 98 is in the same plane as the throat of nozzle 74 with no tension on springs 114. The zeroing operation is accomplished by adjustment of studs 106. The cylindrical scale appropriate to the springs and nozzle used is then placed on scale stud 100. The coefficient of friction $\mu$ between sample 112 and surface 76 of nozzle 74 is determined by testing or by consulting a friction coefficient table. Cylindrical scale 102 is then rotated until the correct coefficient of friction is opposite reference mark 126 and the scale is locked in place by knurled knob 104.

Prior to beginning the extraction process, it is necessary to know the effective thickness $t_e$ of sample 112. Effective thickness is the volume of the sample solid constituents divided by the area of the sample, and it is best determined by the air displacement method using a pychometer or from table of characteristic materials, thicknesses. Once the effective thickness is known, sample 112 is extracted through nozzle 74 by pulling on handle assembly 90 until indicator tab 109 is aligned with the sample effective thickness printed on scale 128. As hereinabove recited, scale 128 has been calibrated for use with nozzle 74 such that when indicator tab 109 is alined with the effective thickness of the sample being tested, a constant packing ratio is achieved in the throat of nozzle 74 regardless of sample thickness. For the embodiment shown in FIGS. 4 and 5, it is preferable that scale 128 be calibrated to yield a packing ratio of 0.07. Scale 130 is similarly calibrated for use with nozzle 122. When indicator tab 109 is alined with the effective thickness of sample 112 as pointed on scale 128, handle assembly 90 is rotated to lock bushing barrel 86 on cylindrical scale 102 and the handle modulus is read from the axial coordinate at reference mark 126.

It should also be noted that the axial coordinate of cylindrical scaler 102 and 124 may be calibrated such that a direct reading of handle modulus ratio ($H/\bar{H}$) is obtained. Calibration of cylindrical scales 102 and 124 is accomplished according to the following equation.

$$H \simeq \frac{K\Delta \left(1 + \frac{5}{4} \frac{r_{o1}}{L}\right)}{A_{on}P_oN_1\left(1 + \mu \frac{N_2}{N_1}\right)}$$

where
K = combined spring rate of springs 114
Δ = elongation of springs 114, and
Δ = displacement of reference mark 126 with respect to the cylindrical scale
$P_o$ = packing ratio = 0.07
$N_1$ = geometric nozzle characteristic
$N_2$ = frictional nozzle characteristic
$A_{on}$ = throat area of the nozzle for which the calibration is made
$r_{o1}$ = throat radius of smallest nozzle to be used with a given handlemeter
L = maximum stroke of handlemeter, and
L = maximum displacement of extraction rod with respect to nozzle throat It should be noted however, that the above calibration equation holds true only for those situations where the extraction rod diameter (d) divided by the throat radius of the smallest nozzle used is less than or equal to unity and where the effective thickness of the sample falls within the following limits:

$$t_{e(min.)} = \left(\frac{\frac{P_o}{2}}{\frac{L}{r_{on}} + \frac{r_{o1}}{2r_{on}}}\right) \frac{1}{r_{on}}$$

$$t_{e(max.)} = \left(\frac{\frac{P_o}{2}}{\frac{L}{4r_{on}} + \frac{r_{o1}}{2r_{on}}}\right) \frac{1}{r_{on}}$$

where
$r_{on}$ = throat radius of the nozzle for which the calibrated scale will be used.

The above calibration equations represent an approximation which yields an error no greater than ±4%. However, if it is desired, one may calculate the exact handle modulus valve by means of the following equation:

$$H = \frac{K\Delta}{A_oN_1\left(1 + \mu \frac{N_2}{N_2}\right)\left(P_o - \frac{d}{r_o} \frac{t_e}{r_o}\right)}$$

Apparatus constructed according to the present invention, therefore, have the capability of measuring the handle of fabric or other flexible materials in the form of a handle modulus or handle modulus ratios. Obviously numerous modifications of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A system for quantitatively measuring the handle of flexible materials comprising:
a nozzle composed of a truncated cone section and an annulus section;
a sample of flexible material to be measured;
means for holding said nozzle;
means for drawing said flexible material sample through the truncated cone and annulus sections of said nozzle;
means for determining a force necessary to draw said flexible material sample through said nozzle; and
means for determining a displacement of said flexible material sample with respect to said nozzle in order to determine a compaction ratio of said flexible material sample in said nozzle.

2. A system as in claim 1 wherein said means for holding said nozzle comprises a frame means for holding said nozzle stationary with respect to said means for drawing said flexible material sample through said nozzle.

3. A system as in claim 2 wherein said frame means is comprised of a base plate, a plurality of axially adjustable leveling studs fixedly attached to said base plate and extending downwardly therefrom, a plurality of legs fixedly attached to said base plate and extending upwardly therefrom, and an upper plate fixedly attached to said plurality of legs and containing an aperture therein for mounting said nozzle.

4. A system as in claim 3 wherein the radius of said circular sample is less than the axial length of said plurality of frame legs.

5. A system as in claim 1 wherein said nozzle comprises a convergent nozzle and said sample of flexible material to be measured is circular in configuration, and said means for drawing said flexible material sample through said nozzle is attached to the center of said circular sample of flexible material.

6. A system as in claim 1 wherein said means for drawing said flexible material sample through said nozzle comprises an extraction rod.

7. A system as in claim 6 wherein one end of said extraction rod is provided with a concave recess, threaded bore, domed washer and cap screw threadably engaging said threaded bore in order to attach said sample of flexible material to said extraction rod.

8. A system as in claim 1 wherein said means for determining the force necessary to draw said flexible material sample through said nozzle and said means for determining the displacement of said flexible material sample with respect to said nozzle comprise a laboratory load-displacement testing machine.

9. A system as in claim 8 wherein:
said nozzle comprises a convergent nozzle;
said means for drawing said flexible material sample through said nozzle comprises an extraction rod;
said sample of flexible material to be measured is circular in configuration;
said extraction rod is attached to the center of said circular sample; and
said means for mounting said nozzle is comprised of a base plate; an attachment fixture means for connecting said base plate to said standard load displacement testing machine; a plurality of axially adjustable leveling studs fixedly attached to said base plate, extending downwardly therefrom and bearing against said standard load-displacement testing machine; a plurality of legs fixedly attached to said base plate and extending upwardly therefrom; and an upper plate means fixedly attached to said plurality of legs and containing an aperture therein for mounting said nozzle.

10. A system as in claim 1 wherein said means for holding said nozzle comprises a hollow two-part cylindrical telescoping assembly comprised of a nozzle section having said nozzle mounting thereon and a handle section concentrically, slidably disposed in said nozzle section.

11. A system as in claim 10 wherein said telescoping nozzle body section and handle body section are provided with means to prevent relative rotation therebetween.

12. A system as in claim 11 wherein said means to prevent relative rotation between said nozzle and handle body sections comprises axial slots in said sections and a plurality of tabs extending radially outward from the edge of said handle body section axial slot and slidably engaging said nozzle body section axial slot.

13. A system as in claim 11 wherein said means to prevent relative rotation between said nozzle and handle body sections comprises a screw threadably engaging said nozzle body section and extending therethrough, said screw slidably engaging a second axial slot in said handle body section.

14. A system as in claim 13 wherein said means for drawing said flexible material sample through said nozzle comprises a cylindrical extraction rod concentrically and slidably disposed in said handle section, and said handle body section is provided with a handle means for assisting manual displacement of said handle body section with respect to said nozzle body section and said extraction rod, and is further provided with means for locking said handle body section with respect to said extraction rod.

15. A system as in claim 14 wherein:
said nozzle comprises a plurality of convergent nozzles;
said sample of flexible material to be tested is circular in configuration;
said means for determining the force necessary to draw said flexible material sample through said nozzle comprises a plurality of coil springs connected to said extraction rod and to said handle body section and further comprises a cylindrical scale rotatably mounted on said extraction rod and plotting the coefficient of friction between said flexible material sample and said nozzle versus handle modulus ratio and a reference mark on said handle body section for use with said cylindrical scale in order to select the proper coefficient of friction and read said handle modulus coordinate; and
said means for determining the displacement of said flexible material sample with respect to said nozzle comprises a reference mark on said extraction rod and a plurality of scales, equal in number to said plurality of convergent nozzles, wherein said plurality of scales are calibrated in terms of the distance necessary to extract flexible material samples of differing thicknesses in order to achieve a compaction ratio of 0.07 at the throat of said plurality of convergent nozzles.

16. A system as in claim 15 wherein the radius of said circular sample is greater than the maximum axial displacement of said extraction rod and wherein said circular sample is attached at its center to said extraction rod.

17. A system as in claim 1 wherein said means for determining the force necessary to draw said flexible material sample through said nozzle comprises spring means connected to said means for drawing said flexible material sample through said nozzle.

18. A system as in claim 17 wherein said spring means comprises a plurality of coil springs further connected to said means for mounting said nozzle, and further comprises a scale affixed to said means for drawing said flexible material sample through said nozzle.

19. A system as in claim 1 wherein said means for determining the force necessary to draw said flexible material sample through said nozzle includes a scale on which the coefficient of friction between said flexible material sample and said nozzle is plotted versus handle modulus, and wherein said means for mounting said nozzle is provided with a reference mark for use with said scale in order to select the proper coefficient of friction and read said handle modulus coordinate.

20. A system as in claim 1 wherein said means for determining the force necessary to draw said flexible material sample through said nozzle includes a scale on which the coefficient of friction between said flexible material sample and said nozzle is plotted versus handle modulus ratio, and wherein said means for mounting said nozzle is provided with a reference mark for use with said scale in order to select the proper coefficient of friction and read said handle modulus ratio coordinate.

21. A system as in claim 1 wherein said means for determining the displacement of said flexible material sample with respect to said nozzle comprises a reference mark on said means for drawing said flexible material sample through said nozzle and a scale.

22. A system as in claim 21 wherein a plurality of said nozzles and an equal plurality of said displacement scales are provided.

23. A system as in claim 1 wherein said means for determining the displacement of said flexible material sample with respect to said nozzle is calibrated in terms of the distance necessary to extract flexible material samples of differing thickness in order to achieve a desired constant compaction ratio at the throat of said nozzle.

24. A method of quantitatively measuring the handle of flexible material comprising:
providing a sample of flexible material to be measured;
providing a nozzle composed of a truncated cone section and an annulus section;
drawing said sample through the truncated cone and annulus sections of said nozzle;
measuring a distance said sample is drawn through said nozzle in order to determine a compaction ratio; and
measuring a force required to draw said sample through said nozzle, whereby the handle modulus of said sample is calculated as a function of the force required to draw said sample through said nozzle, the minimum cross-sectional area at the throat of said nozzle, and the frictional and geometric properties of said nozzle.

25. A method as in claim 24 further comprising:
providing a sample of reference material of wide use to be measured;
dividing the calculated handle modulus of said test sample by the calculated handle modulus of said reference sample to arrive at a non-dimentional handle modulus ratio.

26. A method as in claim 25 wherein the handle modulus of said sample of flexible material to be tested and the handle modulus of said sample of reference material are calculated at equal ratios of sample cross-sectional area to nozzle cross-sectional area at the throat of said nozzle.

27. A method as in claim 26 wherein said handle modulus ratio is calculated by dividing the slope of the force-displacement curve of said sample of flexible material to be tested by the slope of the force-displacement curve of said reference sample.

28. A method as in claim 26 wherein the handle modulus of said sample of flexible material and the handle modulus of said sample of reference material are calculated at a ratio of sample cross-sectional area of nozzle cross-sectional area at the throat of said nozzle is equal to 0.07.

29. A method as in claim 24 wherein the handle modulus of said sample of flexible material to be tested is calculated as a function of slope of the extraction force-displacement curve, the minimum cross-sectional area of said nozzle, the ratio of test sample cross-sectional area to nozzle cross-sectional area at the throat of said nozzle, and the frictional and geometric properties of said nozzle.

30. A method as in claim 24 wherein the handle modulus of said sample of flexible material to be tested is calculated as a function of discrete force and displacement data, the minimum cross-sectional area of said nozzle, the ratio of test sample cross-sectional area to nozzle cross-sectional area at the throat of said nozzle and the frictional and geometric properties of said nozzle.

* * * * *